United States Patent
Hancher et al.

(10) Patent No.: US 7,121,996 B2
(45) Date of Patent: Oct. 17, 2006

(54) SEVERED SPINAL CORD REGENERATION USING NATURAL PROCESSES AND PATIENT'S OWN RESOURCES

(76) Inventors: Donna Hancher, 77 W. Palm Dr., Margate, FL (US) 33063; Nancy Burkle, 2845 NE. 18th Ave., Wilton Manors, FL (US) 33306

( * ) Notice: Subject to any disclaimer, the term of this patent is extended or adjusted under 35 U.S.C. 154(b) by 394 days.

(21) Appl. No.: 10/814,886

(22) Filed: Mar. 31, 2004

(65) Prior Publication Data

US 2004/0199043 A1 Oct. 7, 2004

(51) Int. Cl.
*A61N 2/00* (2006.01)

(52) U.S. Cl. .......................... 600/9; 623/17.11

(58) Field of Classification Search .............. 600/9–15; 128/897–899; 623/17.11, 23.64, 23.72, 23.76, 623/925

See application file for complete search history.

(56) References Cited

U.S. PATENT DOCUMENTS

| | | | |
|---|---|---|---|
| 4,774,967 A | 10/1988 | Zanakis et al. | |
| 4,919,140 A | 4/1990 | Borgens et al. | |
| 4,966,144 A | 10/1990 | Rochkind et al. | |
| 5,925,053 A | 7/1999 | Hadlock et al. | |
| 6,033,660 A | 3/2000 | Mather | |
| 6,132,360 A * | 10/2000 | Halpern | 600/9 |
| 6,167,888 B1 | 1/2001 | Tuszynski et al. | |

* cited by examiner

*Primary Examiner*—John P. Lacyk
(74) *Attorney, Agent, or Firm*—Malin, Haley & DiMaggio, P.A.

(57) ABSTRACT

A method and apparatus for repairing a severed spinal cord using natural processes and patient's own resources, which includes removing cells from the patient, such as embryonic and somatic cells, and a segment of vein from the patient. The vein segment is used to encase the severed portion of the spinal cord. The cultured cells of the patient are injected into the encasement of vein segment surrounding the severed spinal cord. A chip that can generate a magnetic or electric field is then placed on top of the vein to provide a magnetic or electric field on the severed area of the spinal cord that includes the patient's cultured cells. The purpose is to repair spinal cord damage through regeneration using a patient's own cells and magnetic or electromagnetic energy.

4 Claims, 2 Drawing Sheets

SEVERED SPINAL CORD REGENERATION USING NATURAL PROCESSES AND PATIENT'S OWN RESOURCES

BACKGROUND OF THE INVENTION

1. Field of the Invention

This invention relates to a method for repairing the severed spinal cord for regeneration, and specifically, to a process for naturally repairing a severed spinal cord through regeneration.

2. Description of Prior Art

A severed spinal cord is one of most traumatic injuries that a mammal can suffer. Complete loss of motor function and of and neurological feeling is commonplace. As of today very little success has been achieved in repairing a severed spinal cord either through surgery or other methods. U.S. Pat. No. 4,774,967 issued Oct. 4, 1988 shows a method and apparatus for nerve regeneration. The invention provides for the nerve regeneration using electric potential gradient from the proximal into the distal nerve endings with the nerve guide. U.S. Pat. No. 6,033,660 issued Mar. 7, 2000 shows a method of treating nervous system injury with culture and Schwann cells. U.S. Pat. No. 4,919,140 issued Apr. 24, 1990 shows a method and apparatus for regenerating nerves. The system uses an oscillating electric field to the central nervous system across the lesion to stimulate growth of facing axions. U.S. Pat. No. 5,925,053 issued Jul. $20^{th}$ 1999 shows a guidance channel to promote nerve regeneration using Schwann cells. U.S. Pat. No. 4,966,144 issued Oct. 30, 1990 shows a method for inducing regeneration of injured nerve fibers. The injured side of the spinal cord is treated with light. U.S. Pat. No. 6,167,888 issued Jan. 2, 2001 shows a method for inducing partial recovery of lost voluntary motor function after spinal cord injury in a mammal using gene therapy.

Although gene therapy may offer promising results in the future, the present-day treatment of spinal cord injury and still does not provide for significant recovery for patient. The purpose of the present invention is to provide a method for severed spinal cord regeneration using natural processes such as natural energy from a magnet and electric fields.

SUMMARY OF THE INVENTION

This invention comprises a method for repairing a severed spinal cord using natural processes and patient's own resources which includes removing cells from the patient including embryonic and somatic cells and pluripotent cells which are cultured in the lab and a segment of vein from the patient in preparation for providing the repair. The patient's spinal cord at the point of lesion is surrounded by the patient's own segment of vein much like a pipeline connecting both parts of the severed spinal cord together at the lesion site. The cells that were previously drawn and cultured from the patient are then injected into the volume inside the pipeline formed with the patient's vein segment and the severed ends of the spinal cord. A magnetic field is provided across both severed ends of the spinal cord by the use of a small magnet that is attached to the outside of the vein, midway between the lesion between the severed ends of the spinal cord. The magnetic field might be provided by a microchip in which the poles are arranged such that the axis of the magnet for north-south or from south-north is collectively aligned with the center line of the severed spinal cord ends. The magnet may be provided in a microchip in which alternating magnetic fields are applied in oscillating manner. The purpose of the energy provided from the magnetic field is to excite or energize patient's own cells which are then injected in the damaged area which will produce regeneration with the severed ends between the severed ends of the spinal cord.

The pipeline or guidance channel obtained from the patient's own vein or artery (preferably a vein from the leg, the great vein in the leg), is desired. Peripheral and spinal cord fluid pluripotent/embryonic somatic cells can be gathered from the patient and cultured in the lab that can be injected into the inside pipeline formed by the vein with the damaged ends of the spinal cord mounted inside the pipeline.

Protective agents must also be introduced into the vein containing the cells that are under the influence of the magnetic fields. The interaction of the patient's own cells which are natural and the natural effects of the magnetic field energize the cells which are the patient's own cells by electrophoresis. When the cells are excited, the antigens and NT bodies are forced to move towards their respective poles (opposite poles attracting) by countercurrent electrophoresis. The Schwann cells and embryo nerve fibers and spinal fluid will create synapses representing the proper cells adjoining union during activity.

The theory is that within a few days sufficient amounts of energy have been used to promote enough cells to connect peripheral nerves naturally by the positive and negative attraction and the north and south polar attraction caused by the magnetic field. An electric field may also be employed to generate positive and negative attraction. It is thought that the nerves could possibly grow approximately 1 mm per month.

Using the patient's own chemistry created tissue is believed to be the best option for improved results. Obviously each patient condition would be unique and if there were any adverse cell buildup in the artery or the vein used as the pipeline and that situation would have to be dealt with. Protective agents could be introduced to offset any unusual negative situation.

The combination embryonic, somatic and spinal cord cells may create neurons that program the brain to send signals to severed areas.

It is an object of this invention to provide a process for natural repair and regeneration of the severed spinal cord.

It is another object of this invention to provide a method for repairing spinal cord damage through regeneration using the patient's own cells and magnetic and electromagnetic energy.

In accordance with these and other objects which will become apparent hereinafter, the present invention will now be described with particular reference to the accompanying drawings.

PREFERRED EMBODIMENT OF THE INVENTION

Figure 1:
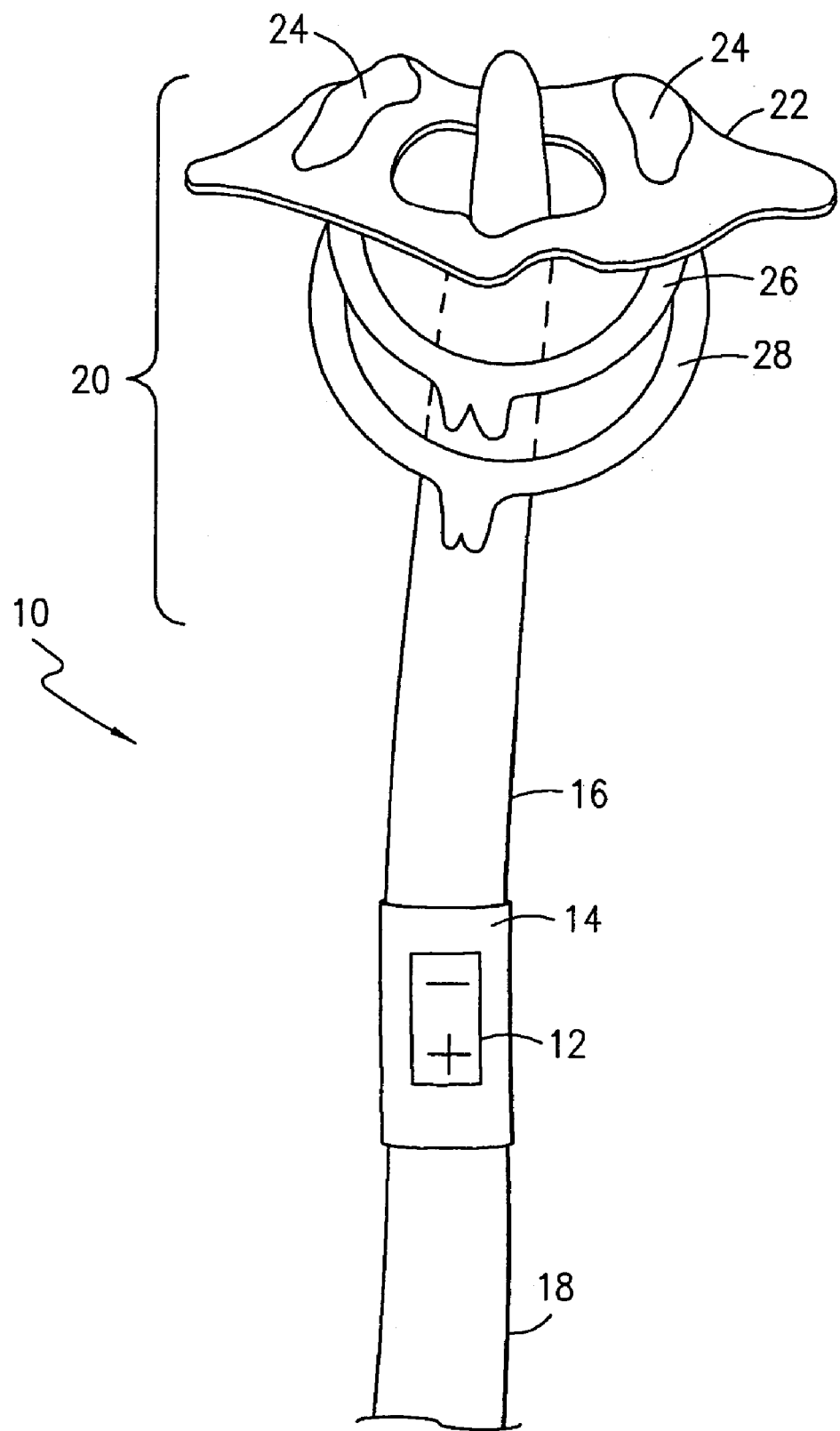
FIG. 1 shows a schematic diagram of an area of spinal cord in a mammal.

Referring now to the drawings and in particular FIG. 1, the environment for the present invention is shown generally at 10 showing a small magnet 12 representing a magnetic microchip attached to vein 14 which represents the patient's ongoing segment that was removed from another part of the patient preferably the patient's leg. Element 16 represents the upper portion of an injured or severed spinal cord of a human mammal. Element 18 represents the lower severed portion of the patients spinal cord. The purpose of the invention is to induce cord regeneration to provide motor function and feeling to the neural system to the patient by the rejoining of the elements 16 and 18 which have been severed. The actual severed cord is not shown in FIG. 1 because it is inside vein 14.

Figure 2:
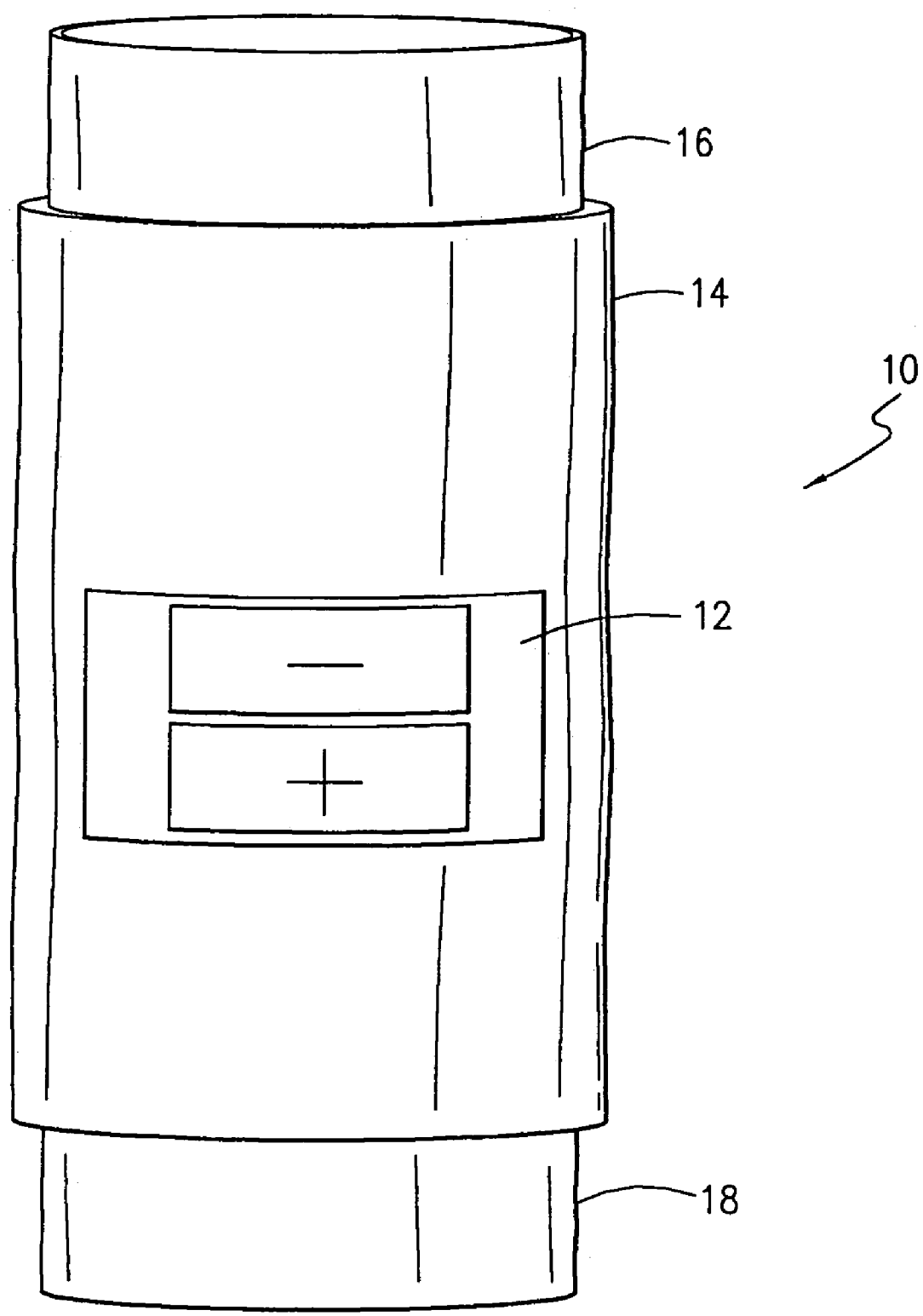
FIG. 2 shows a schematic representation of the segment of the severed spinal cord in accordance with the present invention.

Referring now to FIGS. 1 and 2, the artery or vein 14 is prepared for the designated area on the spinal column between the upper portion 16 and the lower portion 18 to serve as a pipeline. Thus the vein is wrapped around the spinal cord at the area where the spinal cord is severed. The cells from the patient include the somatic cells and pluripotent cells that have been removed from the patient and cultured in a lab. When the cultured cells have replicated enough, the cultured cells are implanted into the designated area between the upper and lower severed portions of the spinal cord 16 and 18, respectively, and inside the vein 14. The magnetic magnet 12, represented by a microchip, is strategically placed on the vein pipeline on the outside of vein 14 to excite the human cells that are injected inside the vein segment. With the help of nature and an energy source, it is believed that the spinal cord area can be healed and can produce neurons that are vital for regeneration.

FIG. 1 shows schematically an area of the central nerve pathway 20 that includes the representative vertebrae 22 termed the atlas and axis vertebrae 26 along with another vertebrae 28, all of which represents schematically a central nerve pathway 20. Also shown are areas 24 which refer to articular facet for occipital condyle.

The guidance channel is formed by the vein 14 that can be either an artery or a vein taken from the leg or from another area preferably the great saphenous vein in the leg. Peripheral and spinal cord fluid pluripotent in embryonic and somatic cells are gathered from the patient and cultured in a lab and may be injected into the damaged area of the spinal cord. Also neuro-protective agents should also be introduced. The titanium magnetic microchip 12 which is placed on top of the artery or vein 14 produces an attraction of atoms. The plus and minus symbols on microchip 12 represent north and south magnetic poles or electric field poles. It is believed that the interaction of the titanium chip or magnet in conjunction with the patient's own cells can be re-energized by electrophoresis. When the patient's injected cells are excited, the antigens and antibodies are forced to move towards their respective poles opposite or towards each other by means of countercurrent electrophoresis. The Schwann cells embryo (myelin sheets) of nerve fibers and spinal fluid create the synapses by presenting the proper cells to join a union while the activity takes place. This is the first and primary objective.

After a few days, it is believed that would be sufficient amounts of energy to promote enough cells to connect peripheral nerves naturally by means of positive and negative attraction of energy. It is believe that the peripheral nerves will grow approximately 1 mm per month. The use of nature cells from the patient's own body chemistry is believed to be the best option for a natural result. Of course, there must be attention to any build up of any adverse cells in the artery or vein 14. Once the cells regenerate, the chip can be removed, if desired.

Thus, in looking at the entire process, the patient's own artery or vein is used, the patient's own cells are used and a natural magnetic field is used from a magnet or from a microchip that can produce a magnetic field or an electric field. All of the elements used in this regeneration process are natural either to the patient or to the forces of nature.

Regeneration by natural methods and patient's own resources is believed to be the best and desired result of treatment of injuries and trauma caused by a severed spinal cord in a mammal.

The present invention has been shown and described herein in what is considered to be the most practical and preferred embodiment. It is recognized, however, that departures may be made therefrom within the scope of the invention and that obvious modifications will occur to a person skilled in the art.

What is claimed is:

1. The method of repairing a severed spinal cord for regeneration comprising the steps of:
    removing cells from the patient including embryonic, somatic and pluripotent and increasing their volume by culturing in a laboratory;
    removing a vein segment from the patient;
    placing the patient's vein segment around the severed area of the spinal cord;
    injecting the removed cultured patient cells into the area of the spinal cord surrounded by the patient's vein segment; and
    placing a magnet on top of said vein segment to subject the severed spinal cord and patient cells to a magnet field.

2. The method as in claim 1 including the steps of: oscillating the magnetic field with an oscillating magnet.

3. The method as in claim 1 wherein the magnet is mounted in a chip that is placed on to the patient's vein segment.

4. The method as in claim 1 including the step of:
    generating an electric field by the magnetic microchip placed on top of the vein in the severed area.

* * * * *